United States Patent [19]

Gsell et al.

[11] Patent Number: 4,786,654
[45] Date of Patent: Nov. 22, 1988

[54] SUBSTITUTED BENZYLCYCLOPROPYLMETHYL ETHERS

[75] Inventors: Laurenz Gsell, Basel; Peter Ackermann, Pfeffingen, both of Switzerland

[73] Assignee: Ciba-Geigy Corporation, Ardsley, N.Y.

[21] Appl. No.: 53,911

[22] Filed: May 26, 1987

[30] Foreign Application Priority Data

Jun. 10, 1986 [CH] Switzerland ............... 2338/86

[51] Int. Cl.$^4$ .............. A01N 31/16; C07C 43/29; C07C 149/34; C07C 147/06
[52] U.S. Cl. .............. 514/712; 514/719; 568/32; 568/49; 568/637; 568/661
[58] Field of Search .............. 568/32, 637, 661, 49; 514/719, 712

[56] References Cited

U.S. PATENT DOCUMENTS

4,054,667 10/1977 Flex ............... 514/719 X
4,575,517 3/1986 Krüger et al. ............... 514/719 X
4,611,004 9/1986 Ackermann et al. ............... 514/464

FOREIGN PATENT DOCUMENTS

59-116243 12/1982 Japan.

*Primary Examiner*—Vivian Garner
*Attorney, Agent, or Firm*—Kevin T. Mansfield; Edward McC. Roberts

[57] ABSTRACT

There are disclosed novel unsubstituted or substituted phenoxyfluorobenzyltetramethylcyclopropylmethyl ethers of formula

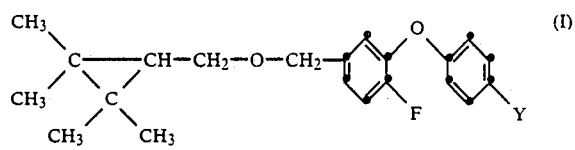

wherein Y is hydrogen, halogen, $C_1$–$C_4$alkyl or $C_1$–$C_4$alkyl which is substituted by 1 to 9 halogen atoms, $C_1$–$C_4$alkoxy or $C_1$–$C_4$alkoxy which is substituted by 1 to 9 halogen atoms, $C_1$–$C_4$alkylthio or $C_1$–$C_4$alkylthio which is substituted by 1 to 9 halogen atoms, or is $C_2$–$C_4$alkenyl or $C_2$–$C_4$alkynyl and their benzyl ether intermediates of formula IV

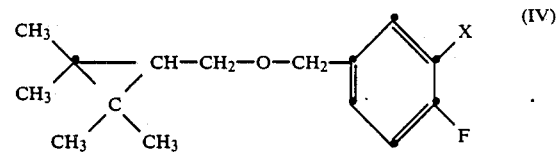

wherein X is halogen or p-tosyl.

Also disclosed is a process for the preparation of these compounds and compositions containing them for use in pest control, especially for controlling insects that attack plants and animals, in particular their larval stages. The novel compounds are particularly effective against plant-destructive insects in rice crops.

11 Claims, No Drawings

SUBSTITUTED BENZYLCYCLOPROPYLMETHYL ETHERS

The present invention relates to novel unsubstituted or substituted (3-phenoxy-4-fluorobenzyl)-(2,2,3,3-tetramethylcyclopropylmethyl)ethers, to the preparation thereof, to intermediates for their synthesis, and to the use thereof in pest control.

The novel ethers of the invention have the formula I

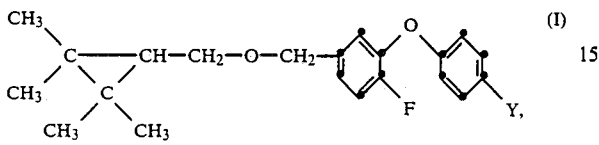

wherein Y is hydrogen, halogen, $C_1$–$C_4$alkyl or $C_1$–$C_4$alkyl which is substituted by 1 to 9 halogen atoms, $C_1$–$C_4$alkoxy or $C_1$–$C_4$alkoxy which is substituted by 1 to 9 halogen atoms, $C_1$–$C_4$alkylthio or $C_1$–$C_4$alkylthio which is substituted by 1 to 9 halogen atoms, or is $C_2$–$C_4$alkenyl or $C_2$–$C_4$alkynyl.

Within the scope of this invention, halogen will be understood as meaning fluorine, chlorine, bromine or iodine, with fluorine or chlorine being preferred.

Alkyl, haloalkyl, alkoxy, haloalkoxy, alkylthio and haloalkylthio groups Y may be in straight chain or branched configuration. Typical examples of such groups are: methyl, trifluoromethyl, methoxy, difluoromethoxy, ethyl, ethoxy, propyl, isopropyl, n-butyl, isobutyl and the like. Preferred alkenyl groups are vinyl, propenyl and allyl.

Compounds of formula I meriting special mention on account of their biological activity are those wherein Y is hydrogen, halogen, $C_1$–$C_3$alkyl, methoxy, ethoxy, methylthio, trifluoromethyl, vinyl, propargyl or ethynyl.

Particularly preferred compounds of formula I are those wherein Y is hydrogen, fluorine, bromine, chlorine, iodine, methyl, methoxy, vinyl and ethynyl, and also those wherein Y is hydrogen, fluorine, methyl or methoxy.

The compounds of formula I are prepared in a manner known per se by (a) reacting the compound of formula II

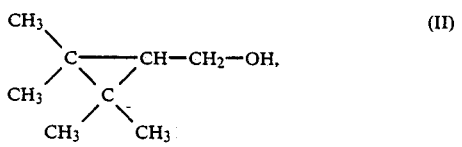

with a compound of formula III

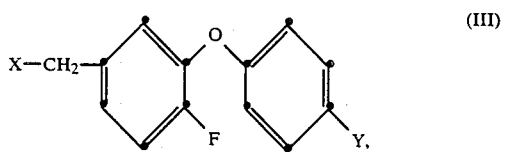

or (b) reacting a compound of formula IV

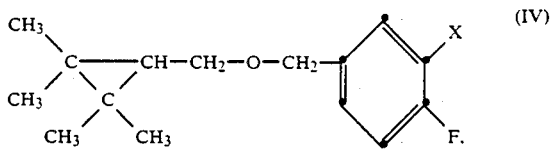

with a compound of formula V

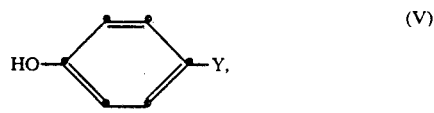

in which formulae II, III, IV and V above Y is as defined for formula I and X is a halogen atom, preferably an iodine or bromine atom, or is the p-tosyl group.

The above processes are carried out in the temperature range from −10° to +120° C., normally from 20° to 80° C., under normal or elevated pressure and preferably in an inert solvent or diluent. Examples of suitable solvents or diluents are: ethers and ethereal compounds, such as diethyl ether, dipropyl ether, dioxane, dimethoxyethane and tetrahydrofuran; amides such as N,N-dialkylated carboxamides; aliphatic, aromatic and halogenated hydrocarbons, preferably benzene, toluene, xylene, chloroform, and chlorobenzene; nitriles such as acetonitrile; dimethyl sulfoxide; and ketones, e.g. acetone, methyl ethyl ketone; and hexane. The etherification of process (a) is conveniently carried out in the presence of a base such as an alkali metal hydroxide or alkali metal carbonate, but preferably a metal hydride, e.g. sodium hydride. The etherification of process (b) to give the diphenyl ether is carried out either under the normal conditions of the Ullmann condensation or in accordance with process (a).

The starting materials of formulae II, III and V are known and can be prepared by methods analogous to known ones. Thus the preparation of the tetramethylcyclopropylmethanol of formula II is described in Tetrahedron Letters 34, 3331–35. The phenoxybenzyl derivatives of the formula III type and the preparation thereof are disclosed in e.g. European patent application No. 0 125 204, GB patent application No. 2 085 006 and in DE-OS No. 2 709 355. The benzyl ethers of formula IV are novel and likewise constitute an object of the present invention. They can be prepared by reacting the tetramethylcyclopropylmethanol of formula II with an appropriately substituted benzyl derivative of formula VI

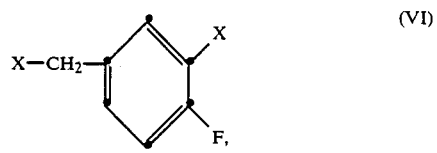

wherein X is as defined above.

It has been found that the compounds of formula I of this invention have excellent properties as pesticides while being well tolerated by plants and having low toxicity to warm-blooded animals. They are particularly suitable for controlling pests that attack plants and animals. In this connection attention is drawn to the very low toxicity of the compounds of this invention to fish—an important aspect for application in rice crops.

In particular, the compounds of formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina.

The good pesticidal activity of the compounds of this invention corresponds to a mortality of at least 50–60% of the above pests.

In addition to their action against mosquitoes and flies, e.g. *Aedes aegypti* and *Musca domestica*, the compounds of formula I are also suitable for controlling plant-destructive feeding insects in ornamentals and crops of useful plants, especially in cotton (e.g. against *Spodoptera littoralis* and *Heliothis virescens*) and in cereals, fruit and vegetables (e.g. against *Laspeyresia pomonella*, *Leptinotarsa decemlineata* and *Epilachna varivestis*). The compounds of formula I are also very effective larval insects stages and nymphs, especially of noxious feeding insects. The compounds of formula I can also be used very successfully against plant-destructive cicadas, especially in rice crops.

The compounds of formula I are also suitable for controlling ectoparasites, e.g. *Lucilia sericata*, as well as ticks on domestic animals and productive livestock, e.g. by treating animals, cowsheds, barns, stables etc., and pastures.

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and *Bacillus thuringiensis* preparations.

The compounds of formula I are used in unmodified form or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in, e.g., polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of the formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used, e.g., for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g., the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g., the sodium or calcium salt of lignosulfonic acid, dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi-(2-chloroethyl)ethylammonium bromide.

The surfactants customarily employed in the art of formulation are described, e.g., in "McCutcheon's Detergents and Emulsifiers Annual", MC Publishing Corp. Ridgewood, N.J. 1979; Dr. Helmut Stache, "Tensid Taschenbuch" (Handbook of Surfactants), Carl Hauser Verlag, Munich/Vienna, 1981.

The pesticidal compositions usually contain—based on weight—0.1 to to 99%, preferably 0.1 to 95%, of a compound of formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

EXAMPLE 1

Preparation of (3-phenoxy-4-fluorobenzyl)-(2,2,3,3-tetramethylcyclopropylmethyl)ether A solution of 1.9 g of 2,2,3,3-tetramethylcyclopropylmethanol and 4.2 g of 3-phenoxy-4-fluorobenzyl bromide in 20 ml of a 1:1 mixture of toluene/dimethylformamide is added dropwise at 0°–5° C. to 0.9 g of sodium hydride (50% dispersion in mineral oil) in 60 ml of a 1:1 mixture of toluene/dimethylformamide. When the reaction has subsided, the batch is stirred for 16 hours at room temperature and, after the dropwise addition of a saturated solution of ammonium chloride, extracted with toluene. The combined toluene extracts are washed with saturated sodium chloride solution, dried over MgSO4 and concentrated by rotary evaporation. The crude product is chromatographed through a column of 300 g of silica gel (elution with a 95:5 mixture of hexane/ether), affording the title compound of formula

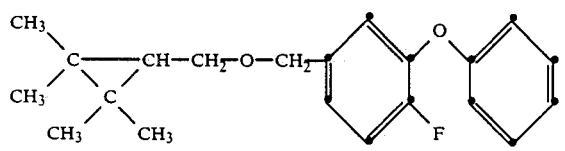

in the form of a clear oil with a refractive index of $n_D^{24} = 1.5300$ (compound 1).

The following compounds of formula I can also be obtained in accordance with the procedure described in this Example:

| Compound | Y | Physical data |
|---|---|---|
| 2 | F | $n_D^{25} = 1.5186$ |
| 3 | —CH$_3$ | $n_D^{25} = 1.5293$ |
| 4 | —Cl | $n_D^{25} = 1.5343$ |

EXAMPLE 2

Preparation of (3-bromo-4-fluorobenzyl)-(2,2,3,3-tetramethylcyclopropylmethyl)ether (starting material of formula IV)

A solution of 20 g of 2,2,3,3-tetramethylcyclopropylmethanol and 41.9 g of 3-bromo-4-fluorobenzyl bromide in 100 ml of a 1:1 mixture of toluene/dimethylformamide is added dropwise at 0°–10° C. to 8.2 g of sodium hydride (50% dispersion in mineral oil) in 200 ml of a 1:1 mixture of toluene/dimethylformamide. When the reaction has subsided, the batch is stirred for 16 hours at room temperature and, after the dropwise addition of a saturated solution of ammonium chloride, extracted with toluene. The combined toluene extracts are washed with saturated sodium chloride solution, dried over MgSO4 and concentrated by rotary evaporation. The crude product is chromatographed through a column of silica gel (elution with a 5:1 mixture of hexane/ether), affording the title compound in the form of a clear oil with a refractive index of $n_D^{24} = 1.5128$.

EXAMPLE 3

Formulations of compounds of formula I according to Example 1 or combinations thereof with other insecticides or acaricides (throughout, percentages are by weight)

| 3.1 Emulsifiable concentrates | (a) | (b) | (c) |
|---|---|---|---|
| active ingredient or active ingredient combination | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsion of any required concentration can be produced from such concentrates by dilution with water.

| 3.2 Solutions | (a) | (b) | (c) | (d) |
|---|---|---|---|---|
| active ingredient or active ingredient combination | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| expoxidised coconut oil | — | — | 1% | 5% |
| ligroin (boiling range 160–190°) | — | — | 94% | — |

These solutions are suitable for application in the form of microdrops.

| 3.3 Granulates | (a) | (b) |
|---|---|---|
| active ingredient or active ingredient combination | 5% | 10% |
| kaolin | 94% | — |
| highly dispersed silicic acid | 1% | — |
| attapulgite | — | 90% |

The active ingredient or active ingredient combination is dissolved in methylene chloride, the solution is sprayed onto the carrier, and the solvent is subsequently evaporated off in vacuo.

| 3.4 Dusts | (a) | (b) |
|---|---|---|
| active ingredient or active ingredient combination | 2% | 5% |
| highly dispersed silicic acid | 1% | 5% |
| talcum | 97% | — |
| kaolin | — | 90% |

Ready for use dusts are obtained by intimately mixing the carriers with the active ingredient or active ingredient combination.

EXAMPLE 4

Action against *Musca domestica*

50 g of freshly prepared CMSA nutrient substrate for maggots are charged into each of a number of beakers. A specific amount of an acetonic solution containing 1% by weight of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at the given concentration. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

Compounds of formula I according to Example 1 exhibit good activity in this test.

EXAMPLE 5

Action against *Aedes aegypti*

A concentration of 200 ppm is obtained by pipetting a specific amount of a 0.1% solution of the test compound in acetone onto the surface of 150 ml of water in a beaker. After the acetone has evaporated. 30 to 40 two-day old larvae of *Aedes aegypti* are put into the beaker containing the test compound. Mortality counts are made after 2 and 7 days.

Compounds of formula I according to Example 1 exhibit good activity in this test.

EXAMPLE 6

Action against *Laodelphax striatellus* and *Nilaparvata lugens* (nymphs)

The test is carried out with growing plants. For this purpose 4 rice plants (thickness of stem 8 mm) about 20 cm in height are planted into each of a number of pots (diameter 8 cm). The plants in each pot are sprayed on a rotary table with 100 ml of an acetonic solution containing 400 ppm of the respective test compound. After the spray coating has dried, each plant is populated with 20 nymphs of the test organisms in the third stage. To prevent the cicadas from escaping, a glass cylinder open at both ends is slipped over each of the plants and sealed with a gauze top. The nymphs are kept for 10 days on the treated plant until the next development stage has been reached. Evaluation of percentage mortality is made 1, 4 and 8 days after treatment.

Compounds of formula I according to Example 1 exhibit good activity in this test.

EXAMPLE 7

Ovicidal action against *Laodelphax striatellus* and *Nilaparvata lugens*

The test is carried out with growing plants. For this purpose 4 rice plants (thickness of stem 8 mm; height about 20 cm) are planted into each of a number of pots (diameter 8 cm).

The plants in each pot are sprayed on a rotary table with 100 ml of an acetonic solution containing 400 ppm of the respective test compound. After the spray coating has dried, each plant is populated with 3 adult females. To prevent the females from escaping, a glass cylinder is slipped over each of the plants and sealed with a gauze top. The females are left on the treated plant for 4 days for oviposition and are then removed.

About 8 days after the females have been placed on the plants, the young cicadas hatch from the eggs and a count is made. The percentage mortality is calculated by comparing the number of larvae which have hatched on the treated plants with the number which have hatched on the untreated control plants.

Compounds of formula I according to Example 1 exhibit good ovicidal activity in this test.

EXAMPLE 8

Insecticidal action against feeding insects

Cotton plants about 25 cm high, in pots, are sprayed with aqueous emulsions which contain the respective test compound in a concentration of 400 ppm. After the spray coating has dried, the cotton plants are populated with *Spodoptera littoralis* and *Heliothis virescens* larvae in the $L_1$-stage. The test is carried out at 24° C. and 60% relative humidity. The percentage mortality of the test insects is determined after 120 hours in comparison with untreated controls.

In the above test, compound 1 according to Example 1 effected 80–100% kill against *Spodoptera larvae*.

EXAMPLE 9

Action against *Nephotettix cincticeps* (nymphs)

The test is carried out with growing plants. For this purpose approximately twenty-day-old rice plants about 15 cm in height are planted into each of a number of pots (diameter: 5.5 cm).

The plants in each pot are sprayed on a rotary table with 100 ml of an acetonic solution containing 400 ppm of the test compound. After the spray coating has dried, each plant is populated with 20 nymphs of the test organisms in the second or third stage. To prevent the cicadas from escaping, a plexiglass cylinder is slipped over each of the plants and sealed with a gauze top. The nymphs are kept for 5 days on the treated plants, which have to be watered at least once. The test is carried out at a temperature of about 23° C. and at 55% relative humidity. The plants are exposed to light for a period of 16 hours per day.

The compounds of Example 1 are very effective in this test.

EXAMPLE 10

Action against *Bemisia tabaci*

Cotton plants in the cotyledon stage, in pots, are populated with *Bemisia tabaci* (white flies) such that 40 unsexed adults are present on each plant. After oviposition over 3 days, all adults are removed. Ten days after infestation, i.e. at a time when about two-thirds of the nymphs are in the 1st nymphal stage and one third are in the 2nd nymphal stage, the infested plants are sprayed to drip point with an aqueous formulation of the test compound (concentration: 400 ppm). A count of dead and living nymphs, pupae and adults is made 24 days after infestation. The test is carried out in a greenhouse compartament at 25° C. and at a relative humidity of about 50–60%.

The compounds of formula I of Example 1 are very effective in this test.

What is claimed is:

1. A compound of formula I

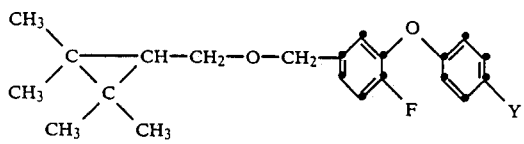

wherein Y is hydrogen, halogen, $C_1$–$C_4$alkyl or $C_1$–$C_4$alkyl which is substituted by 1 to 9 halogen atoms, $C_1$–$C_4$alkoxy or $C_1$–$C_4$alkoxy which is substituted by 1 to 9 halogen atoms, $C_1$–$C_4$alkylthio or $C_1$–$C_4$alkylthio which is substituted by 1 to 9 halogen atoms, or is $C_2$–$C_4$alkenyl or $C_2$–$C_4$alkynyl.

2. A compound of formula I according to claim 1, wherein Y is hydrogen, halogen, $C_1$–$C_3$alkyl, methoxy, ethoxy, methylthio, trifluoromethyl, vinyl, propargyl or ethynyl.

3. A compound of formula I according to claim 2, wherein Y is hydrogen, fluorine, bromine, chlorine, iodine, methyl, methoxy, vinyl and ethynyl.

4. A compound of formula I according to claim 3, wherein Y is hydrogen, fluorine, bromine, chlorine, iodine or methyl.

5. A compound according to claim 4 of formula

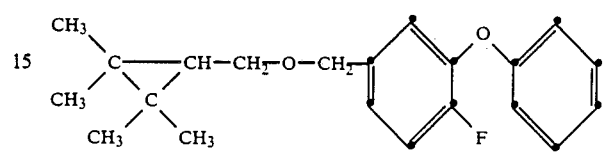

6. A compound of formula IV

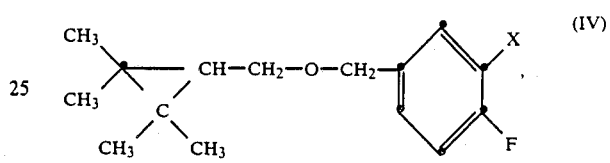

wherein X is halogen or the p-tósyl group.

7. A pesticidal composition which contains a pesticidally effective amount of a compound as claimed in claim 1, together with suitable carriers and/or other adjuvants.

8. A method of controlling insects and representatives of the order Acarina, which comprises treating or contacting said pests, their various development stages and/or the locus thereof, with a pesticidally effective amount of a compound of formula I according to claim 1, or with a composition which contains a pesticidally effective amount of a compound according to claim 1, together with adjuvants and carriers suitable therefor.

9. A method according to claim 8 for controlling insects and representatives of the order Acarina that are pests of animals and plants.

10. A method according to claim 9 for controlling plant-destructive insects.

11. A method according to claim 10 for controlling plant-destructive insects in rice crops.

* * * * *